(12) United States Patent
Bae et al.

(10) Patent No.: US 10,687,964 B2
(45) Date of Patent: Jun. 23, 2020

(54) INTERVERTEBRAL IMPLANT WITH INTEGRATED FIXATION

(71) Applicant: Howmedica Osteonics Corp., Mahwah, NJ (US)

(72) Inventors: Hyun Bae, Santa Monica, CA (US); Nicholas Slater, Chandler, AZ (US); Joshua A. Butters, Chandler, AZ (US); Daniel F. Justin, Orlando, FL (US); Dylan Hushka, Chandler, AZ (US); Rick B. Delamarter, Los Angeles, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 7 days.

(21) Appl. No.: 15/645,298

(22) Filed: Jul. 10, 2017

(65) Prior Publication Data

US 2017/0333218 A1    Nov. 23, 2017

Related U.S. Application Data

(63) Continuation of application No. 13/389,298, filed as application No. PCT/US2010/044988 on Aug. 10, 2010, now Pat. No. 9,700,434.

(Continued)

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/447* (2013.01); *A61F 2/4455* (2013.01);
(Continued)

(58) Field of Classification Search
CPC ........ A61F 2/4611; A61F 2/4455; A61F 2/44; A61F 2/442; A61F 2/46; A61F 2/447;
(Continued)

(56) References Cited

U.S. PATENT DOCUMENTS 3,486,505 A  12/1969  Morrison
3,641,590 A  2/1972  Michele
(Continued)

FOREIGN PATENT DOCUMENTS

EP  0179695 A1  4/1986
EP  1327423 A1  7/2003
(Continued)

OTHER PUBLICATIONS

International Search Report and Written Opinion, PCT/US2010/22494, dated Oct. 25, 2010.
(Continued)

*Primary Examiner* — Tessa M Matthews
(74) *Attorney, Agent, or Firm* — Lerner, David, Littenberg, Krumholz & Mentlik, LLP

(57) ABSTRACT

A surgical instrument and method for inserting a spinal implant in the intervertebral disc space between two adjacent vertebrae and an anchor engageable with the implant and an adjacent vertebra are provided. The instrument includes an inserter having an engagement portion including a distal engagement surface for interfacing with the implant and a handle portion. The engagement portion includes a track for slidably translating the anchor toward the engagement surface. A kit is provided including the inserter and a tamp to force the anchor into engagement with the implant and the adjacent vertebra. The kit may also include a cutter for piercing the adjacent vertebra.

16 Claims, 11 Drawing Sheets

Related U.S. Application Data

(60) Provisional application No. 61/257,734, filed on Nov. 3, 2009, provisional application No. 61/257,667, filed on Nov. 3, 2009, provisional application No. 61/232,705, filed on Aug. 10, 2009, provisional application No. 61/232,745, filed on Aug. 10, 2009.

(52) U.S. Cl.
CPC ..... *A61F 2/30734* (2013.01); *A61F 2002/305* (2013.01); *A61F 2002/30166* (2013.01); *A61F 2002/30172* (2013.01); *A61F 2002/30352* (2013.01); *A61F 2002/30367* (2013.01); *A61F 2002/30387* (2013.01); *A61F 2002/30401* (2013.01); *A61F 2002/30528* (2013.01); *A61F 2002/30593* (2013.01); *A61F 2002/30736* (2013.01); *A61F 2002/30738* (2013.01); *A61F 2002/30841* (2013.01); *A61F 2002/30845* (2013.01); *A61F 2002/30879* (2013.01); *A61F 2002/30884* (2013.01); *A61F 2002/30904* (2013.01); *A61F 2002/4627* (2013.01); *A61F 2002/4629* (2013.01); *A61F 2220/0025* (2013.01); *A61F 2220/0033* (2013.01); *A61F 2230/0028* (2013.01); *A61F 2230/0052* (2013.01)

(58) Field of Classification Search
CPC ........ A61F 2/30734; A61F 2002/30166; A61F 2002/30172; A61F 2002/30352; A61F 2002/30377; A61F 2002/30387; A61F 2002/30401; A61F 2002/30504; A61F 2002/30528; A61F 2002/30736; A61F 2002/30738; A61F 2002/30841; A61F 2002/30845; A61F 2002/30848; A61F 2002/30879; A61F 2002/30884; A61F 2002/30904; A61F 2002/4475; A61F 2002/4627; A61F 2002/4629
See application file for complete search history.

(56) References Cited

U.S. PATENT DOCUMENTS

| | | | |
|---|---|---|---|
| 4,047,524 | A | 9/1977 | Hall |
| 4,501,269 | A | 2/1985 | Bagby |
| 4,681,589 | A | 7/1987 | Tronzo |
| 4,743,262 | A | 5/1988 | Tronzo |
| 4,820,305 | A | 4/1989 | Harms et al. |
| 4,834,757 | A | 5/1989 | Brantigan |
| 4,946,378 | A | 8/1990 | Hirayama et al. |
| 5,192,327 | A | 3/1993 | Brantigan |
| 5,306,309 | A | 4/1994 | Wagner et al. |
| 5,314,477 | A | 5/1994 | Marnay |
| 5,431,658 | A | 7/1995 | Moskovich |
| 5,443,514 | A | 8/1995 | Steffee |
| 5,443,515 | A | 8/1995 | Cohen et al. |
| 5,507,816 | A | 4/1996 | Bullivant |
| 5,514,180 | A | 5/1996 | Heggeness et al. |
| 5,609,635 | A | 3/1997 | Michelson |
| 5,683,394 | A | 11/1997 | Rinner |
| 5,702,449 | A | 12/1997 | McKay |
| 5,709,683 | A | 1/1998 | Bagby |
| 5,713,899 | A | 2/1998 | Marnay et al. |
| 5,885,299 | A | 3/1999 | Winslow et al. |
| 5,893,889 | A | 4/1999 | Harrington |
| 6,039,762 | A | 3/2000 | McKay |
| 6,096,080 | A | 8/2000 | Nicholson et al. |
| 6,113,638 | A | 9/2000 | Williams et al. |
| 6,120,503 | A | 9/2000 | Michelson |
| 6,235,059 | B1 | 5/2001 | Benezech et al. |
| 6,241,769 | B1 | 6/2001 | Nicholson et al. |
| 6,325,805 | B1 | 12/2001 | Ogilvie et al. |
| 6,336,928 | B1 | 1/2002 | Guerin et al. |
| 6,364,880 | B1 | 4/2002 | Michelson |
| 6,432,107 | B1 | 8/2002 | Ferree |
| 6,447,524 | B1 | 9/2002 | Knodel et al. |
| 6,447,546 | B1 | 9/2002 | Bramlet et al. |
| 6,582,468 | B1 | 6/2003 | Gauchet |
| 6,679,887 | B2 | 1/2004 | Nicholson et al. |
| 6,716,245 | B2 | 4/2004 | Pasquet et al. |
| 6,726,720 | B2 | 4/2004 | Ross et al. |
| 6,740,118 | B2 | 5/2004 | Eisermann et al. |
| 6,743,256 | B2 | 6/2004 | Mason |
| 6,767,367 | B1 | 7/2004 | Michelson |
| 6,800,093 | B2 | 10/2004 | Nicholson et al. |
| 7,048,766 | B2 | 5/2006 | Ferree |
| 7,056,344 | B2 | 6/2006 | Huppert et al. |
| 7,056,345 | B2 | 6/2006 | Kuslich |
| 7,060,097 | B2 | 6/2006 | Fraser et al. |
| 7,118,580 | B1 * | 10/2006 | Beyersdorff .......... A61F 2/4425 606/99 |
| 7,128,761 | B2 | 10/2006 | Kuras et al. |
| 7,204,852 | B2 | 4/2007 | Marnay et al. |
| 7,235,101 | B2 | 6/2007 | Berry et al. |
| 7,320,707 | B2 | 1/2008 | Zucherman et al. |
| 7,331,995 | B2 | 2/2008 | Eisermann et al. |
| 7,364,589 | B2 | 4/2008 | Eisermann |
| 7,503,934 | B2 | 3/2009 | Eisermann et al. |
| 7,503,935 | B2 | 3/2009 | Zucherman et al. |
| 7,588,600 | B2 | 9/2009 | Benzel et al. |
| 7,594,931 | B2 | 9/2009 | Louis et al. |
| 7,611,538 | B2 | 11/2009 | Belliard et al. |
| 7,658,766 | B2 | 2/2010 | Melkent et al. |
| 7,695,516 | B2 | 4/2010 | Zeegers |
| 7,749,271 | B2 | 7/2010 | Fischer et al. |
| 7,763,076 | B2 | 7/2010 | Navarro et al. |
| 7,842,088 | B2 | 11/2010 | Rashbaum et al. |
| 7,896,919 | B2 | 3/2011 | Belliard et al. |
| 8,021,403 | B2 | 9/2011 | Wall et al. |
| 8,034,076 | B2 | 10/2011 | Criscuolo et al. |
| 8,083,796 | B1 * | 12/2011 | Raiszadeh ............... A61F 2/442 623/17.11 |
| 3,100,974 | A1 | 1/2012 | Duggal et al. |
| 8,747,412 | B2 | 6/2014 | Bae et al. |
| 9,730,807 | B2 * | 8/2017 | Donaldson ............... A61F 2/447 |
| 9,925,051 | B2 * | 3/2018 | Bae ....................... A61F 2/3859 |
| 2002/0004683 | A1 | 1/2002 | Michelson |
| 2002/0035400 | A1 | 3/2002 | Bryan et al. |
| 2002/0165613 | A1 | 11/2002 | Lin et al. |
| 2003/0045940 | A1 | 3/2003 | Eberlein et al. |
| 2003/0195517 | A1 | 10/2003 | Michelson |
| 2003/0195632 | A1 | 10/2003 | Foley et al. |
| 2004/0059318 | A1 | 3/2004 | Zhang |
| 2004/0148028 | A1 | 7/2004 | Ferree et al. |
| 2004/0176853 | A1 | 9/2004 | Sennett et al. |
| 2004/0199254 | A1 | 10/2004 | Louis et al. |
| 2004/0220668 | A1 | 11/2004 | Eisermann et al. |
| 2004/0220670 | A1 | 11/2004 | Eisermann et al. |
| 2004/0230307 | A1 | 11/2004 | Eisermann |
| 2004/0260286 | A1 | 12/2004 | Ferree |
| 2005/0004672 | A1 | 1/2005 | Pafford et al. |
| 2005/0033435 | A1 | 2/2005 | Belliard et al. |
| 2005/0043802 | A1 | 2/2005 | Eisermann et al. |
| 2005/0143820 | A1 * | 6/2005 | Zucherman ........ A61B 17/1671 623/17.11 |
| 2005/0149192 | A1 | 7/2005 | Zucherman et al. |
| 2005/0149193 | A1 | 7/2005 | Zucherman et al. |
| 2005/0165408 | A1 * | 7/2005 | Puno ................... A61F 2/4611 606/99 |
| 2005/0192586 | A1 | 9/2005 | Zucherman et al. |
| 2005/0216081 | A1 * | 9/2005 | Taylor ...................... A61F 2/44 623/17.11 |
| 2006/0004453 | A1 | 1/2006 | Bartish et al. |
| 2006/0085071 | A1 | 4/2006 | Lechmann et al. |
| 2006/0089656 | A1 | 4/2006 | Allard et al. |
| 2006/0116769 | A1 | 6/2006 | Marnay et al. |
| 2006/0129238 | A1 | 6/2006 | Paltzer |
| 2006/0136063 | A1 | 6/2006 | Zeegers |
| 2006/0178745 | A1 | 8/2006 | Bartish et al. |
| 2006/0195097 | A1 * | 8/2006 | Evans ................... A61F 2/4611 606/86 A |

(56) References Cited

U.S. PATENT DOCUMENTS

| | | |
|---|---|---|
| 2006/0212121 A1 | 9/2006 | Ferree |
| 2007/0050032 A1 | 3/2007 | Gittings et al. |
| 2007/0050033 A1 | 3/2007 | Reo et al. |
| 2007/0055378 A1 | 3/2007 | Ankney et al. |
| 2007/0118145 A1 | 5/2007 | Fischer et al. |
| 2007/0123985 A1* | 5/2007 | Errico .................. A61B 17/025 623/17.11 |
| 2007/0233244 A1 | 10/2007 | Lopez et al. |
| 2007/0233261 A1 | 10/2007 | Lopez et al. |
| 2007/0239278 A1 | 10/2007 | Heinz |
| 2007/0270968 A1 | 11/2007 | Baynham et al. |
| 2008/0015702 A1 | 1/2008 | Lakin et al. |
| 2008/0051901 A1 | 2/2008 | de Villiers et al. |
| 2008/0051902 A1 | 2/2008 | Dwyer |
| 2008/0097435 A1 | 4/2008 | DeRidder et al. |
| 2008/0109005 A1 | 5/2008 | Trudeau et al. |
| 2008/0154377 A1 | 6/2008 | Voellmicke |
| 2008/0249575 A1 | 10/2008 | Waugh et al. |
| 2008/0269756 A1 | 10/2008 | Tomko et al. |
| 2009/0005870 A1 | 1/2009 | Hawkins et al. |
| 2009/0088849 A1 | 4/2009 | Armstrong et al. |
| 2009/0105832 A1* | 4/2009 | Allain ................ A61B 17/0642 623/17.16 |
| 2009/0138015 A1 | 5/2009 | Conner et al. |
| 2009/0164020 A1 | 6/2009 | Janowski et al. |
| 2010/0004747 A1 | 1/2010 | Lin |
| 2010/0185292 A1 | 7/2010 | Hochschuler et al. |
| 2010/0211119 A1 | 8/2010 | Refai et al. |
| 2011/0160866 A1 | 6/2011 | Laurence et al. |
| 2011/0196494 A1 | 8/2011 | Yedlicka et al. |
| 2012/0078371 A1* | 3/2012 | Gamache .............. A61F 2/4465 623/17.16 |
| 2012/0078373 A1 | 3/2012 | Gamache et al. |
| 2012/0215315 A1* | 8/2012 | Hochschuler ......... A61F 2/4455 623/17.16 |
| 2012/0253406 A1 | 10/2012 | Bae et al. |
| 2015/0202051 A1* | 7/2015 | Tanaka .................... A61F 2/447 623/17.16 |

FOREIGN PATENT DOCUMENTS

| | | |
|---|---|---|
| EP | 1790298 A1 | 5/2007 |
| EP | 1872746 A2 | 1/2008 |
| WO | 03039400 A2 | 5/2003 |
| WO | 03053290 A1 | 7/2003 |
| WO | 2003092507 A2 | 11/2003 |
| WO | 2004071359 A1 | 8/2004 |
| WO | 2004080355 A1 | 9/2004 |
| WO | 2004108015 A2 | 12/2004 |
| WO | 2005051243 A2 | 6/2005 |
| WO | 2006033067 A3 | 3/2006 |
| WO | 2006051547 A2 | 5/2006 |
| WO | 2006074414 A2 | 7/2006 |
| WO | 2006086494 A2 | 8/2006 |
| WO | 2007087366 A2 | 8/2007 |
| WO | 2008014453 A2 | 1/2008 |
| WO | 2008021955 A2 | 2/2008 |
| WO | 2010028045 A1 | 3/2010 |

OTHER PUBLICATIONS

International Search Report and Written Opinion for Application No. PCT/US2010/055259, dated Apr. 7, 2011.

European Search Report dated Sep. 26, 2012 for PCT/US2010022494.

Extended European Search Report for Application No. EP16171066 dated Dec. 14, 2016.

* cited by examiner

INTERVERTEBRAL IMPLANT WITH INTEGRATED FIXATION

CROSS-REFERENCE TO RELATED APPLICATIONS

The present application is a continuation of U.S. patent application Ser. No. 13/389,298, now U.S. Pat. No. 9,700,434, filed on Feb. 7, 2012, which is a national phase entry under 35 U.S.C. § 371 of International Application No. PCT/US10/44988 filed Aug. 10, 2010, published in English, which claims priority from U.S. Provisional Patent Application No. 61/232,705 filed Aug. 10, 2009, entitled Intervertebral implant with integrated fixation, U.S. Provisional Patent Application No. 61/232,745 filed Aug. 10, 2009, entitled Intervertebral implant with integrated fixation, U.S. Provisional Patent Application No. 61/257,734 filed Nov. 3, 2009, entitled Intervertebral implant with integrated fixation including an instrument for implant revision, and U.S. Provisional Patent Application No. 61/257,667 filed Nov. 3, 2009, entitled Intervertebral implant with integrated fixation, the disclosures of which are hereby incorporated herein by reference.

BACKGROUND OF THE INVENTION

The present invention relates to spinal surgery. More particularly, the present invention relates to surgical instruments and a method of using such instruments to insert an implant and anchors into the intervertebral disc space and the adjacent vertebrae.

Back pain can be caused by many different things, including any one of several problems that affect the intervertebral discs of the spine. These disc problems include, for instance, degeneration, bulging, herniation, thinning of a disc, and abnormal movement, and the pain that is experienced is generally attributable to friction or pressure that inevitably occurs when one adjacent vertebra exerts uneven pressure or when both adjacent vertebrae exert such pressure on the disc. Oftentimes, disc problems lead to the vertebrae impinging on one of the very many nerves located in the spinal column.

One surgical method commonly utilized to correct such disc problems is a fusion procedure where a surgeon fuses together adjacent vertebrae in single or multiple levels. Different methods (as well as apparatus for use in those methods) for such surgery have been developed for performance on cervical, thoracic, or lumbar vertebral bodies. These fusion procedures will be referred to herein as interbody fusion or "IF." Traditional IF techniques generally involve removing at least a portion of the troublesome disc from the patient, adding bone graft material into the interbody space between the vertebrae that flank the disc, and inserting a spinal implant device into the space to hold the graft material in place and to support the vertebrae while solid bone mass forms therebetween. Oftentimes, the steps of inserting an implant and bone graft material involve first packing the implant with the bone graft material, and thereafter implanting that construct.

While IF is a long-established technique for correcting the aforementioned disc problems, it is one that is constantly updated. For instance, different implants have been created to suit specific needs, and methods involving the insertion of such implants and the preparation of the vertebrae to receive same are constantly evolving. One major issue that has existed and will continue to exist is the fact that implants inserted into the disc space often take an extended period of time to achieve permanent fusion between the adjacent vertebrae. This leads to long recovery periods for the patient. Certain implants also fail to achieve a degree of fusion that permanently eliminates flexion, extension, and axial movement between the two adjacent vertebrae. This may allow for the initial fusion created by the implant to wear down in certain aspects, which in turn allows for future discomfort to the patient and potentially follow-up surgical procedures.

Thus, there exists a need for a spinal implant, method of using the implant, and related instrumentation for such method that improves upon these shortcomings.

BRIEF SUMMARY OF THE INVENTION

A first aspect of the present invention is a surgical instrument for inserting a spinal implant in the intervertebral disc space between two adjacent vertebrae and an anchor engageable with the implant and an adjacent vertebra comprising an engagement portion including a superior surface, an inferior surface, a distal engagement surface for interfacing with the implant, and a track on at least one of the superior and inferior surfaces for slidably translating the anchor toward the engagement surface, and a handle portion connected to the engagement portion having a proximal surface for impaction.

In accordance with certain embodiments of this first aspect, the instrument may include a rod extending from the engagement surface. The rod may be threadably engageable with a corresponding aperture in the implant. The handle portion may include a knob connected with the rod for threading the rod into the aperture in the implant. The engagement surface may be curved according to the contour of the implant. The instrument may further include a shoulder extending from at least one of the superior and inferior surfaces of the engagement portion. The instrument may further include connection features on lateral sides of the engagement portion for connection to additional surgical instruments. The connection features may include channels. The track may be embedded within the surface. The track may include a first track on the superior surface and a second track on the inferior surface. The first and second tracks may each include a pair of tracks on the respective surface.

A second aspect of the present invention is a kit of surgical instruments for inserting a spinal implant in the intervertebral disc space between two adjacent vertebrae and an anchor engageable with the implant and an adjacent vertebra comprising an inserter having an engagement portion and a handle portion, the engagement portion including a superior surface, an inferior surface, a distal engagement surface for interfacing with the implant, and a track on at least one of the superior and inferior surfaces for slidably translating the anchor toward the engagement surface, and the handle portion connected to the engagement portion and having a proximal surface for impaction, and a tamp slidably engageable with the inserter in contact with the anchor to force the anchor into engagement with the implant and the adjacent vertebra.

In accordance with certain embodiments of this second aspect, the kit may further include a cutter slidably engageable with the inserter for piercing an adjacent vertebra, the cutter having at least one blade edge for cutting bone. The tamp and the cutter may be slidably mountable within channels on the inserter. The tamp and the cutter may be slidably mountable within the track. The tamp and the cutter may each include a proximal surface for impaction. The tamp may include at least one blade edge for cutting bone.

A third aspect of the present invention is a method of inserting an implant in the intervertebral disc space between two adjacent vertebrae and an anchor engageable with the implant and an adjacent vertebra comprising the steps of attaching a distal end of an inserter to the implant, inserting the implant into the disc space by manipulating the inserter, inserting an anchor into engagement with the implant and the adjacent vertebra, and sliding a tamp along the inserter in contact with the anchor to force the anchor into engagement with the implant and the adjacent vertebra.

In accordance with certain embodiments of this third aspect, the step of sliding the tamp may include impacting a proximal end of the tamp. The method may further include the step of cutting an entryway into the adjacent vertebra for the anchor by sliding a cutter along the inserter and piercing the opposing adjacent vertebra. The method may further include the step of cutting an entryway into the adjacent vertebra for the anchor by sliding the tamp along the inserter and piercing the opposing adjacent vertebra. The step of attaching may include securing the implant to the distal end of the inserter by inserting a rod of the inserter into an aperture of the implant. The step of inserting the rod may include screwing a threaded portion of the rod into a threaded portion of the aperture. The step of screwing may include tightening the threaded rod by way of a knob disposed at a handle of the inserter. The step of inserting the implant may include impacting a proximal end of the inserter. The step of inserting the anchor may include locking the anchor to the implant to prevent migration and backout of the anchor with respect to the implant. The step of inserting the anchor may include locking the anchor to the adjacent vertebra to prevent migration and backout of the anchor with respect to the adjacent vertebra. The anchor may prevent axial movement an axis of the spine between the implant and the adjacent vertebra along. The anchor may prevent torsional movement between the implant and the adjacent vertebra.

In accordance with additional embodiments of the third aspect, the method may further include the steps of inserting a second anchor into engagement with the implant and the opposing adjacent vertebra, and sliding the tamp along the inserter in contact with second anchor to force the anchor into engagement with the implant and the opposing adjacent vertebra. The method may further include cutting an entryway into the opposing adjacent vertebra for the second anchor by sliding a cutter along the inserter and piercing the opposing adjacent vertebra. The method may further include inserting third and fourth anchors into engagement with the implant and adjacent vertebrae such that two anchors are engaged at a superior surface of the implant and two anchors are engaged at an inferior surface of the implant. The method may further include the step of preparing the intervertebral disc space by removing at least a portion of the intervertebral disc. The method may further include packing a chamber of the implant with graft material. The method may further include the steps of providing a kit of differently sized and shaped implants and anchors, and selecting an implant and an anchor according to the anatomy of the patient.

DETAILED DESCRIPTION

Figure 7:
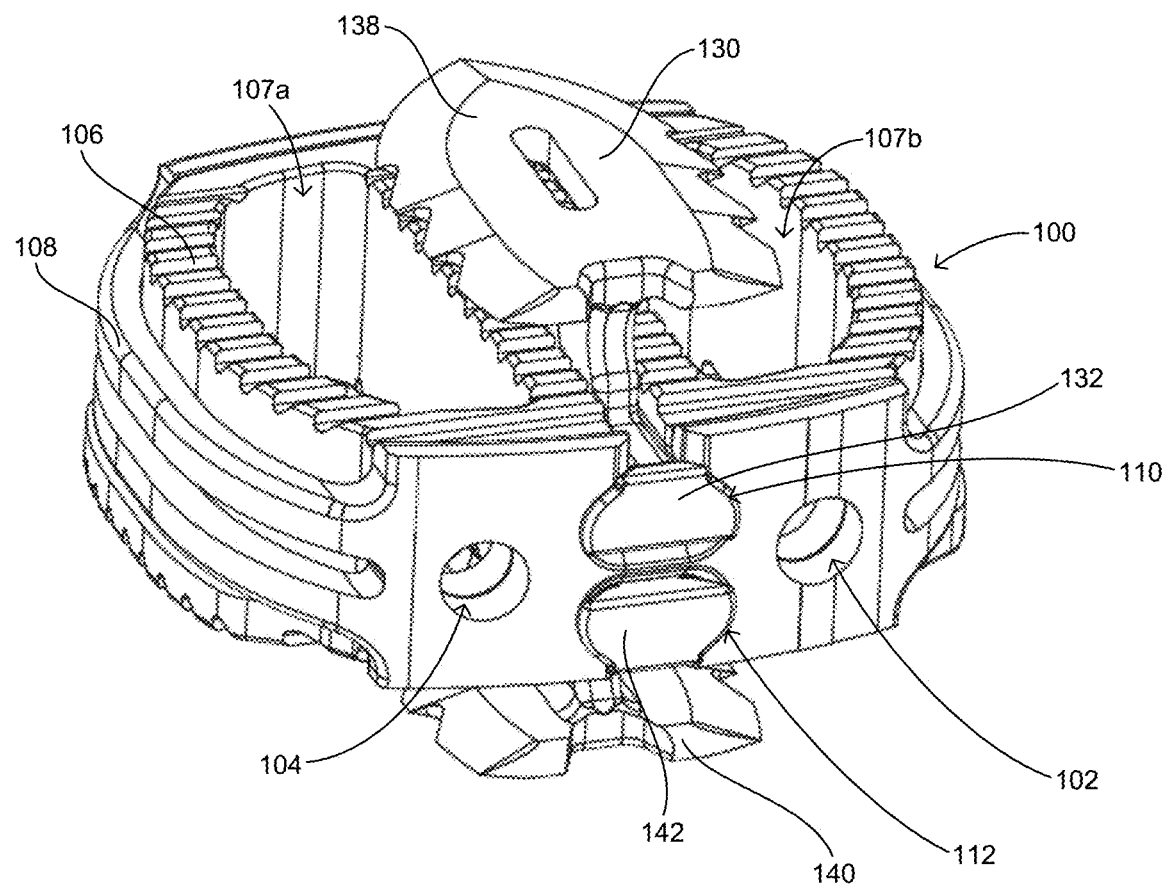
FIG. 7 is a perspective view of the implant and two anchors shown in FIG. 6.
Figure 8:
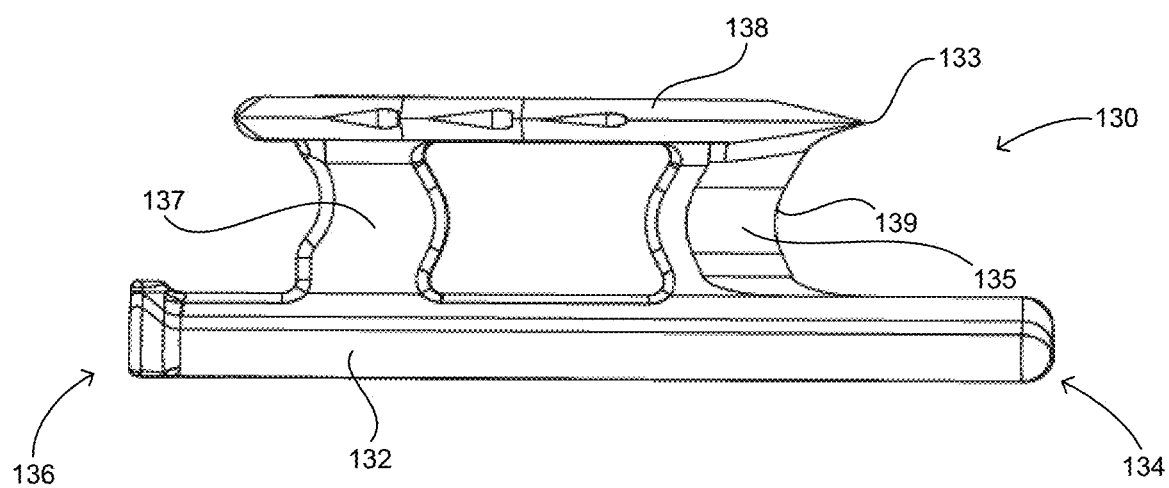
FIG. 8 is a side elevational view of the anchor shown in FIG. 1.

In accordance with a first embodiment of the present invention, a set of instruments is shown in FIGS. 1-5 that are configured for installation of an implant 100 and anchors 130, 140 shown alone in FIGS. 7 and 8. The instruments include an inserter 200, a pilot cutter 300, and an anchor tamp 400.

By way of reference to certain aspects of the below-described instruments, FIGS. 7 and 8 show implant 100 and anchors 130, 140, which are described more thoroughly in U.S. Non-Provisional patent application Ser. Nos. 12/640,816, 12/640,860, and 12/640,892, the disclosure of which is hereby incorporated by reference herein in its entirety. Implant 100 includes, for example, a spacer 106 and a jacket 108 disposed thereabout to provide added strength and support for implant 100. Spacer 106 includes chambers 107a, 107b that can be packed with graft material. Anchor 130 is essentially identical to anchor 140 and is configured to engage the vertebral bodies adjacent the intervertebral disc space in which implant 100 is inserted. In the implanted position, anchors 130, 140 are disposed on opposite sides of the spacer 100. Implant 100 includes interconnection features 110, 112 that extend across spacer 106 and jacket 108 to mate with interconnection portions 132, 142 of anchors 130, 140, respectively. Interconnection portions 132, 142 preferably transmit tension, compression, shear, torsion, and bending loads between anchors 130, 140 and implant 100, so that spinal loads are distributed from one vertebra to another through anchors 130, 140 and across leading and trailing portions of jacket 108. Anchor 130 is generally elongate with a leading end 134 and a trailing end 136 opposite therefrom, with interconnection portion 132 extending therebetween. Interconnection portion 132 is shaped and sized to mate with interconnection feature 110 of implant 100, so as to slidably connect anchor 130 with implant 100. Anchor 130 further includes a fixation portion 138 configured as a plate extending between leading and trailing ends 134, 136. Anchor 130 also includes legs 135, 137 extending generally perpendicularly between interconnection portion 132 and fixation portion 138. Leg 135, which is disposed toward leading end 134 of anchor 130, includes a cutting edge 139 and a piercing tip 133 capable of cutting through bone.

Inserter 200 is capable of attaching securely to implant 100 and placing it into the intervertebral disc space, delivering the anchors 130, 140, and guiding pilot cutter 300 and anchor tamp 400. Inserter 200 is an elongate instrument that includes a body 214 having a proximal end 202 (best shown in FIG. 3A) and a distal end 204. At distal end 204, inserter 200 includes a concavely-curved surface 206 that is preferably shaped to match the curvature of implant 100. Surface 206 can be planar or otherwise shaped to more accurately match the contours of the implant with which it is utilized. A smooth pin 210 extends from surface 206 that interfaces with an appropriately sized aperture 102 on implant 100 to locate and couple implant 100 to inserter 200. Pin 210 is preferably dimensioned to correspond with aperture 102 such that a tight fit is formed therebetween. A threaded rod 212 is disposed between proximal end 202 and distal end 204 and runs through body 214 of inserter 200. Rod 212 is engaged with a threaded aperture 104 of implant 100 and is controlled by a thumb wheel 216 (best shown in FIG. 3A) located at proximal end 202 of inserter 200 that allows the user to tighten implant 100 to face 208 of inserter 200, thus securing implant 100 rigidly in all six degrees of freedom with respect to inserter 200.

Figures 3A, 3B:
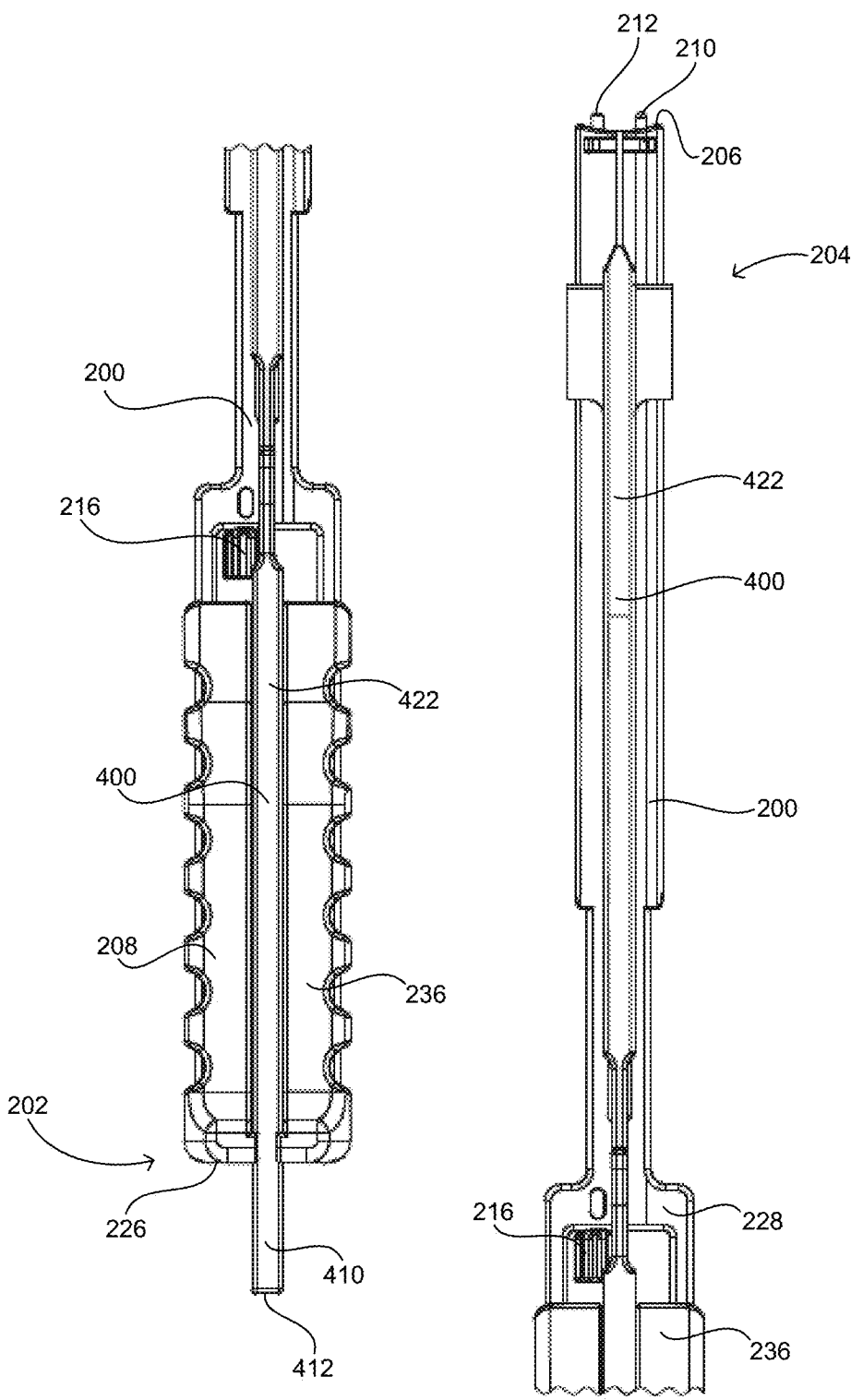
FIGS. 3A and 3B are top plan views of the proximal and distal ends, respectively, of the inserter and tamp shown in FIG. 1.

As shown in FIG. 3A, proximal end 202 of inserter 200 includes a handle 208 and a large face 226 capable of withstanding blows from a mallet to facilitate insertion of implant 100 when impaction is required. A surgeon may grasp and control the instrument at handle 208 without his/her hand or fingers coming into contact with soft tissues of the cervical spine during use of inserter 200.

Inserter 200 has a superior longitudinal channel 218 and an inferior longitudinal channel 220 located on superior surface 228 and inferior surface 230, respectively, of inserter 200 and being capable of containing, aligning, and slidably delivering anchors 130, 140 to engage with implant 100 and the adjacent vertebral bodies once implant 100 is inserted into the disc space. Inserter 200 also includes flanges 222, 224 on a lateral side of inserter 200 that define a channel 223 capable of slidably mating with conforming features on cutter 300 and tamp 400 to allow for translation along a longitudinal axis of inserter 200. Similar flanges and a channel are disposed on the opposed lateral side of inserter 200.

Also at its distal end 204, inserter 200 includes a pair of shoulders 232a, 232b on superior surface 228 and a similar pair of shoulders 234a, 234b on inferior surface 230. Shoulders 232a, 232b, 234a, 234b are configured to engage with cutter 300 and tamp 400 to provide a stop for preventing such instruments and implant 100 from advancing too far into the intervertebral space or adjacent vertebral bodies. Each pair of shoulders is disposed on the respective superior and inferior surfaces 228, 230 so as not to cover or otherwise obstruct longitudinal channels 218, 220. Each shoulder also has a height adjacent channels 218, 220 that corresponds with the dimensions of anchors 130, 140 such that anchors 130, 140 may pass shoulders 232a, 232b, 234a, 234b without coming into contact with same.

Inserter 200 is preferably at least somewhat symmetrical about a horizontal plane parallel to and extending between superior and inferior surfaces 228, 230 such that inserter 200 may be utilized in the orientation depicted or in an inverted orientation. As implant 100 possesses a similar symmetry, inserter 200 can be connected with implant 100 in either orientation. In that regard, it is also beneficial that aperture 102 of implant 100 be threaded as well as threaded aperture 104 so that inserter 200 can be properly engaged and locked to implant 100 in either orientation. Of course, smooth pin 210 of inserter 200 can be configured to engage a aperture, threaded or not, to aid in securing and orienting implant 100 with respect to inserter 200. Inserter 200 is also preferably at least somewhat symmetrical about a vertical plane that bisects superior and inferior surfaces 228, 230.

Inserter 200 is preferably constructed of metal, and may include two or more metals. For example, body 214 may be constructed of stainless steel while handle 208 is constructed of titanium, which may be color anodized. Of course any other material suitable for use during surgery may be employed in the construction of inserter 200. Preferably, the materials utilized in the construction of inserter 200 are capable of being sterilized multiple times, so that the inserter may be utilized in multiple surgeries/procedures.

Figure 4:
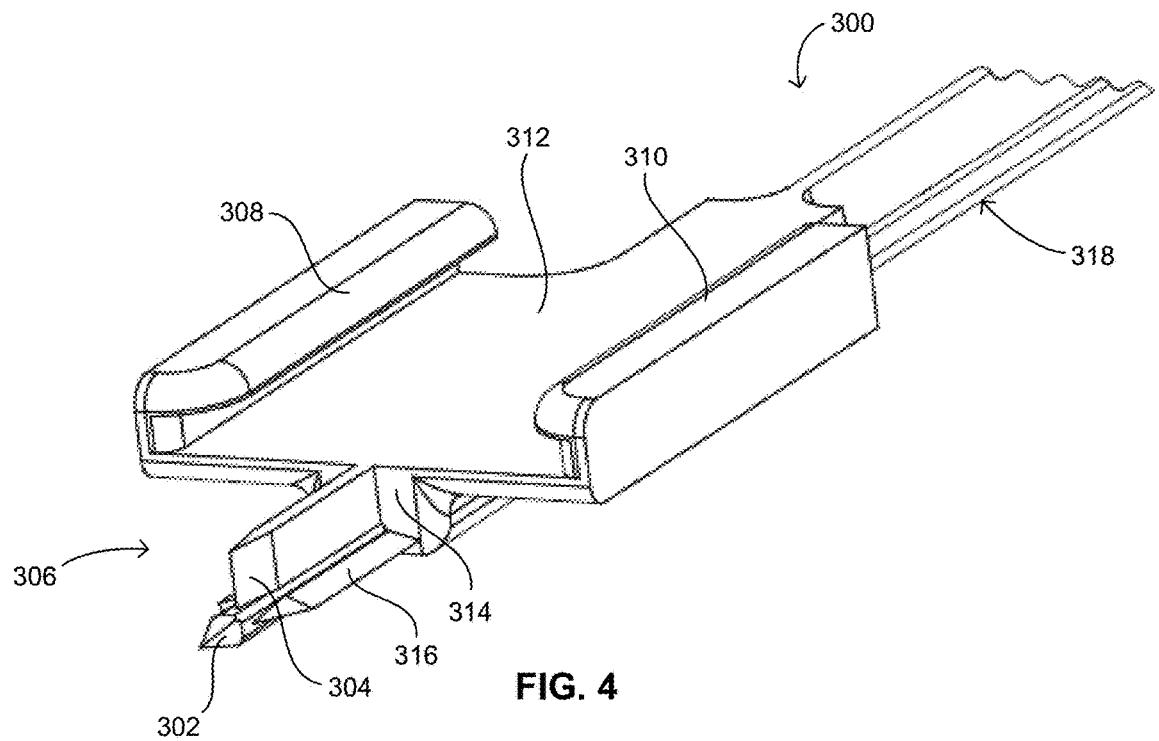
FIG. 4 is a perspective view of the distal end of a pilot cutter in accordance with the first embodiment.

Shown in FIG. 4, cutter 300 is an elongate instrument preferably constructed of stainless steel, and is primarily used for cutting an initial pathway through the vertebral bodies, through which anchors 130, 140 can be led. In particular, cutter 300 is configured to cut a starter channel with minimal force, thereby reducing the total amount of trauma to the vertebral bodies as anchors 130, 140 continue to penetrate the bone. On a distal end 306, cutter 300 includes a blade surface 304 and a trocar-type needle tip 302 extending distally from a front face 314. Additional blades, such a blade 316, can be positioned about blade surface 304 and needle tip 302 as necessary to aid in cutting the vertebral bodies. Multiple blade surfaces or needle tips may also be included as necessary according to the construction of the associated implant and anchors. Blade surface 304 is similar in geometry to cutting edge 139 of anchor 130, minimizing the total force required to insert anchor 130. Needle tip 302 is also geometrically similar to piercing tip 133.

Cutter 300 includes wings 308, 310 extending from a main body 312 that engage with channels, such as channel 223, in inserter 200 to allow for sliding engagement between cutter 300 and inserter 200 to control the path of the cutter 300 during insertion. Front face 314 is configured to abut shoulders 232a, 232b or 234a, 234b during use of cutter 300 to prevent overextending cutter 300 into the vertebral bodies. Once mated with inserter 200, cutter 300 may be impacted on a surface (not shown) at its proximal end, such surface being disposed adjacent to and preferably proximally of face 226 of proximal end of inserter 200. Impaction of the surface at the proximal end of cutter 300 aids in forcing blade surface 304, needle tip 302, and blade 316 into the bone.

Cutter 300 includes a surface 318 along main body 312 that is disposed generally parallel to superior surface 228 or inferior surface 330 when cutter 300 is engaged with inserter 200. Handle 208 of inserter 200 may include a surface 236, as shown in FIG. 3A, that extends above superior surface 228 (or alternatively, inferior surface 330) such that surface 318 of cutter 300 and surface 236 of handle 208 may be substantially coplanar when cutter 300 is engaged with inserter 200. Thus, a surgeon may grasp the combination of cutter 300 and inserter 200 at handle 208, and main body 312 of cutter 300 will not protrude from handle 208, which might make grasping the instruments awkward or uncomfortable. This configuration also allows cutter 300 to easily translate with respect to inserter 200 during impaction of cutter 300 while the surgeon maintains his or her grip around handle 208.

Figure 5:
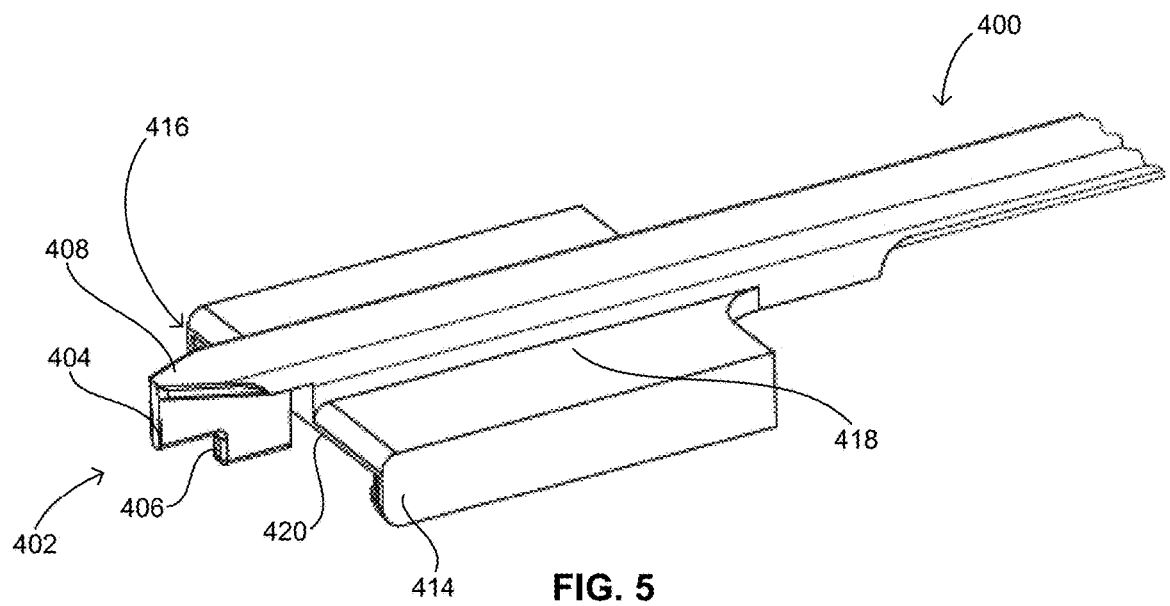
FIG. 5 is a perspective view of the distal end of the tamp shown in FIG. 1.

As shown in FIG. 5, tamp 400 is an elongate, thin instrument constructed of stainless steel, and is used primarily for the insertion of anchors 130, 140 into the vertebral bodies. Tamp 400 includes a distal end 402 that matches the conforming geometry on the proximal end of anchor 130, and more particularly, with respect to the proximal portions of leg 137 and fixation portion 138. When assembled to the inserter 200, tamp 400 engages the proximal end of anchor 130 to controllably push anchor 130 into the vertebral body. Distal end 402 includes a lead edge 404, a secondary edge 406, and an angled top portion 408. Lead edge 404 and angled top portion 408 are configured to mate with leg 137 and fixed portion 138, while secondary edge 406 is configured to mate with the proximal end of interconnection element 132, which extends further proximally than the other components of anchor 130. The mating surfaces between tamp 400 and anchor 130 can be of any configuration as long as tamp 400 may push anchor 130 distally when force is exerted at a proximal end 410 of tamp 400. Tamp 400 may conform to the mating surfaces of anchor 130 or it may not. As described below with respect to the second embodiment, tamp 400 may be provided with appropriate cutting edges to operate as both a cutter and a tamp. Of course, in such a case, the tamp would first be utilized to cut the bone and thereafter utilized to insert the anchors in place.

Tamp 400 includes wings 414, 416 extending from a main body 418, and wings 414, 416 engage channels, such as channel 223, in inserter 200 in a similar manner as cutter 300. Thus, sliding engagement is permitted between tamp 400 and inserter 200 to control the path of tamp 400 during insertion. A front face 420 is also included at distal end 402 of tamp 400 and is configured to abut shoulders 232a, 232b or 234a, 234b during use of tamp 400 to prevent overinsertion of anchors 130, 140 into the vertebral bodies. Once mated with inserter 200, tamp 400 may be impacted similarly to cutter 300 on an impaction surface 412 at proximal end 410, as shown in FIG. 3A. Impaction of surface 412 aids in forcing distal end 402 of tamp 400, and accordingly, anchors 130, 140 into the bone.

Also similar to cutter 300, tamp 400 includes a surface 422 along main body 418 that is disposed generally parallel to superior surface 228 or inferior surface 330 when tamp 400 is engaged with inserter 200. Surface 422 and surface 236 of handle 208 may be substantially coplanar when tamp 400 is engaged with inserter 200. Thus, a surgeon may grasp the combination of tamp 400 and inserter 200 at handle 208, and main body 418 will not protrude from handle 208, which might make grasping the instruments awkward or uncomfortable. Instead, tamp 400 may easily translate with respect to inserter 200 during impaction of tamp 400 while the surgeon maintains his or her grip around handle 208.

A method of inserting implant 100 may begin with a surgeon being provided with a kit of differently sized and shaped implants and anchors and the surgeon selecting a particular implant and corresponding anchors according to the anatomy of the patient upon which the surgical procedure is to be performed. Selected implant 100 is then attached to distal end 204 of inserter 200. Preferably, smooth pin 210 is inserted into aperture 102 of implant to secure implant 100 to inserter 200 in a particular orientation. Threaded rod 212 may also or alternatively be inserted into threaded aperture 104 for additional attachment. Threaded rod 212 may be screwed into aperture 104 by the surgeon actuating thumb wheel 216 disposed at handle 208. Implant 100 and inserter 200 are now secured to one another such that manipulation of inserter 200 can ensure proper positioning of implant within the disc space.

The intervertebral disc space is prepared by removing at least a portion of the intervertebral disc material. This can be done at this stage of the procedure or prior to the surgeon's selection or attachment of implant 100. With the appropriate portion of the disc space cleared, the surgeon aligns and inserts implant 100 into the disc space by manipulating inserter 200, preferably at handle 208 to allow for the area adjacent the disc space to remain free and clear so that the procedure can be appropriately observed. If necessary, face 226 at proximal end 202 of inserter 200 may be impacted by a surgical mallet or other device to allow for proper insertion and position of implant 100 between the adjacent, often collapsed, vertebrae. To further aid in fusing implant 100 to the adjacent vertebrae, one or both of chambers 107a, 107b may be packed with bone graft material prior to insertion of implant 100 within the disc space.

Entryways for anchors 130, 140 are then cut into the adjacent vertebrae. While distal end 204 of inserter 200 is still engaged to implant 100 and positioned adjacent to the disc space, cutter 300 is slidably attached to inserter 200 with wings 308, 310 disposed in channel 223 and a channel on the opposing lateral surface of inserter 200. Cutter 300 is advanced toward the respective vertebra and needle tip 302, blade surface 304, and blade 316 are used to pierce an entryway into the bone. A surgical mallet or other device may be used to strike a proximal end of cutter 300 protruding proximally of handle 208 to assist in preparing the entryway in the bone. Front face 314 preferably contacts shoulders 232a, 232b to prevent cutter from being inserted too far into the vertebra, although it is not necessary that cutter 300 be inserted to a depth that requires contact between front face 314 and shoulders 232a, 232b. Cutter 300 is then disengaged from the bone and inserter 200.

Anchor 130 is then loaded into longitudinal channel 218, which can also be described as a track on superior surface 228. Interconnection element 132 is disposed within channel 218, and tamp 400 is slidably attached to inserter 200 proximal of anchor 130 with wings 414, 416 disposed in channel 223 and a channel on the opposing lateral surface of inserter 200. Inserter 200 may be alternatively configured to allow for side loading of anchor 130 so that tamp 400 may be pre-attached to inserter 200. At least lead edge 404, and preferably secondary edge 406, contact trailing end 136 of anchor 130. As tamp 400 is advanced toward the vertebra, it forces anchor 130 along with it and eventually into contact with the bone. The maintained alignment of inserter 200 with the vertebra and the configuration of cutter 300 ensure that anchor 130 is aligned with the pre-cut entryway as it contacts the bone. Tamp 400 is further advanced to fully insert anchor 130 into the vertebra such that interconnection element 132 of anchor 130 locks into place within interconnection feature 110 of implant 100. Shoulders 232a, 232b may abut front face 420 of tamp 400 during advancement to ensure that anchor 130 is not over-inserted. Anchor 130 is eventually seated such that migration and backout are prevented between anchor 130 with respect to both implant 100 and the adjacent vertebra. Thus, axial and torsional movement between implant 100 and the adjacent vertebra are prevented.

Figure 1:
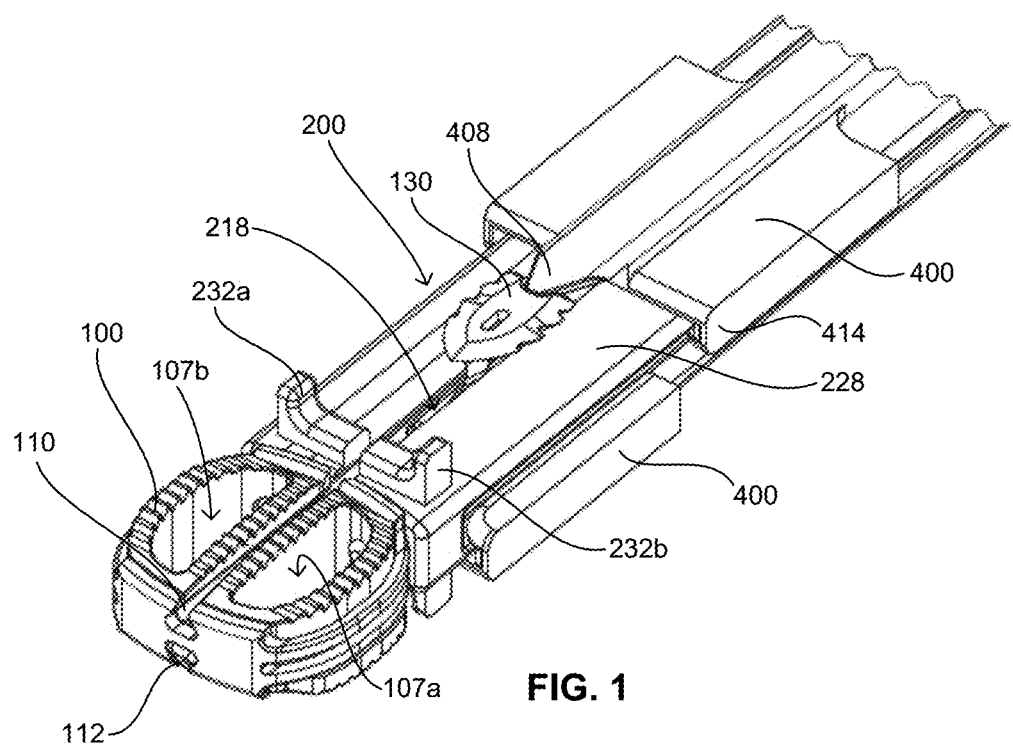
FIG. 1 is a perspective view of an implant and an anchor connected to an insertion instrument having an inserter and two tamps in accordance with a first embodiment of the present invention.
Figure 2:
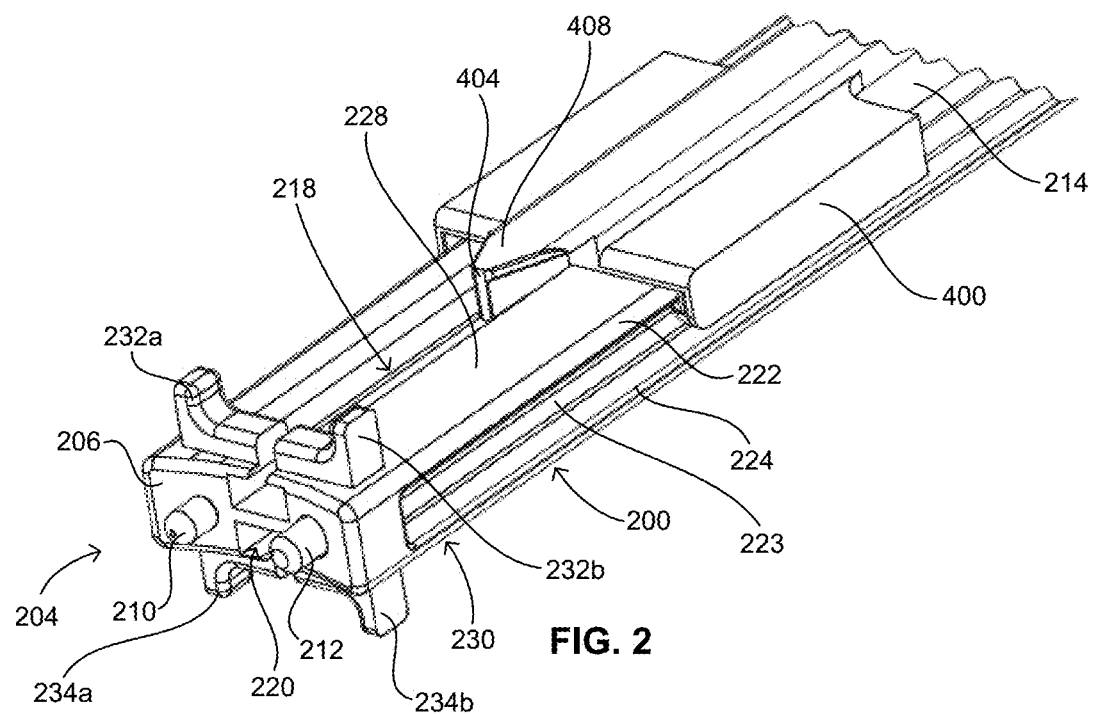
FIG. 2 is a perspective view of the inserter and a tamp shown in FIG. 1.

Anchor 140 may be inserted in the same manner as described above, although with respect to inferior face 230 of inserter 200. Cutter 300 may be used sequentially or two cutters 300 may be utilized and employed simultaneously to cut the respective entryways. Likewise, tamp 400 may be used first on anchor 130 and subsequently on anchor 140, or two tamps 400 may be utilized together, such as shown in FIG. 1. It is noted that tamp 400 and pilot cutter 300 are generally restrained in 5 degrees of freedom with respect to inserter 200 during insertion.

Figure 6:
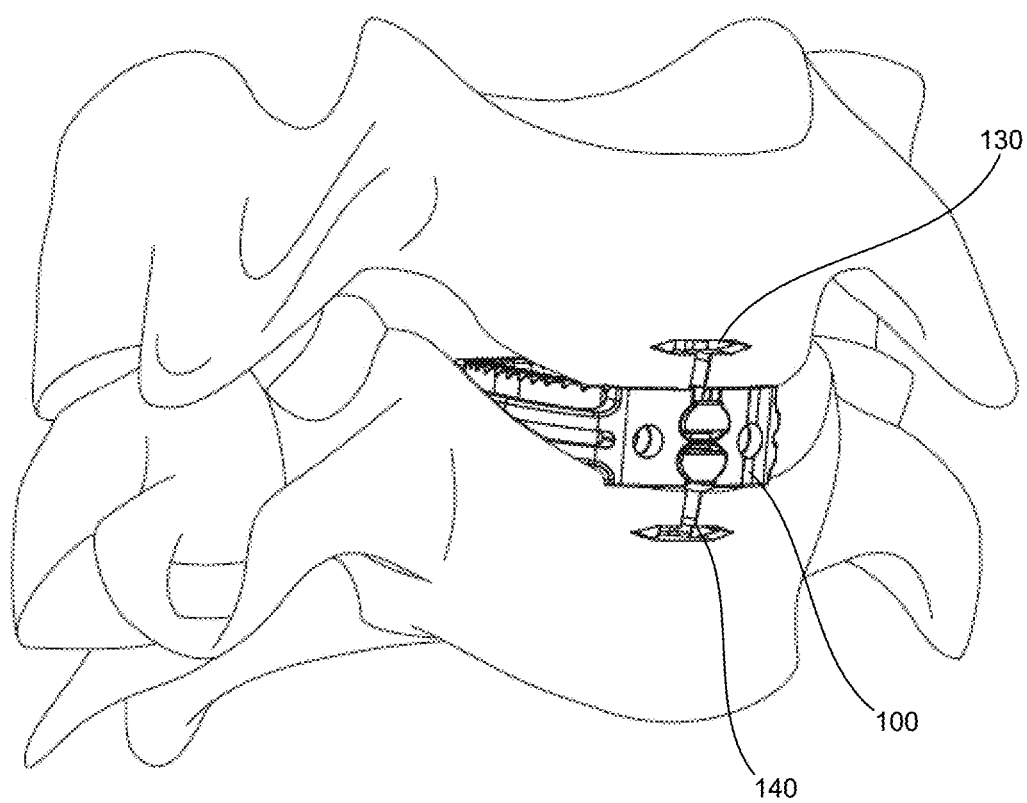
FIG. 6 is a perspective view of the implant and two anchors shown in FIG. 1 inserted into an intervertebral disc space between two adjacent vertebrae.

After tamp 400 is disengaged from inserter 200, threaded rod 212 is unthreaded from implant 100, again using thumb wheel 216. Inserter 200 is then removed from the surgical site, leaving implant 100 and anchors 130, 140 in position as shown in FIG. 6. When implant 100 and anchors 130, 140 are implanted from an anterior approach, as shown in FIG. 6, the leading portion of jacket 108 is positioned in the posterior portion of the intervertebral disc space and the trailing portion of jacket 108 is positioned in the anterior portion of the intervertebral disc space. In this arrangement, prosthesis implant 100 and anchors 130, 140 may replicate the strength and stiffness of the natural anterior and posterior longitudinal ligaments to provide superior fixation of adjacent vertebral bodies.

Figure 14:
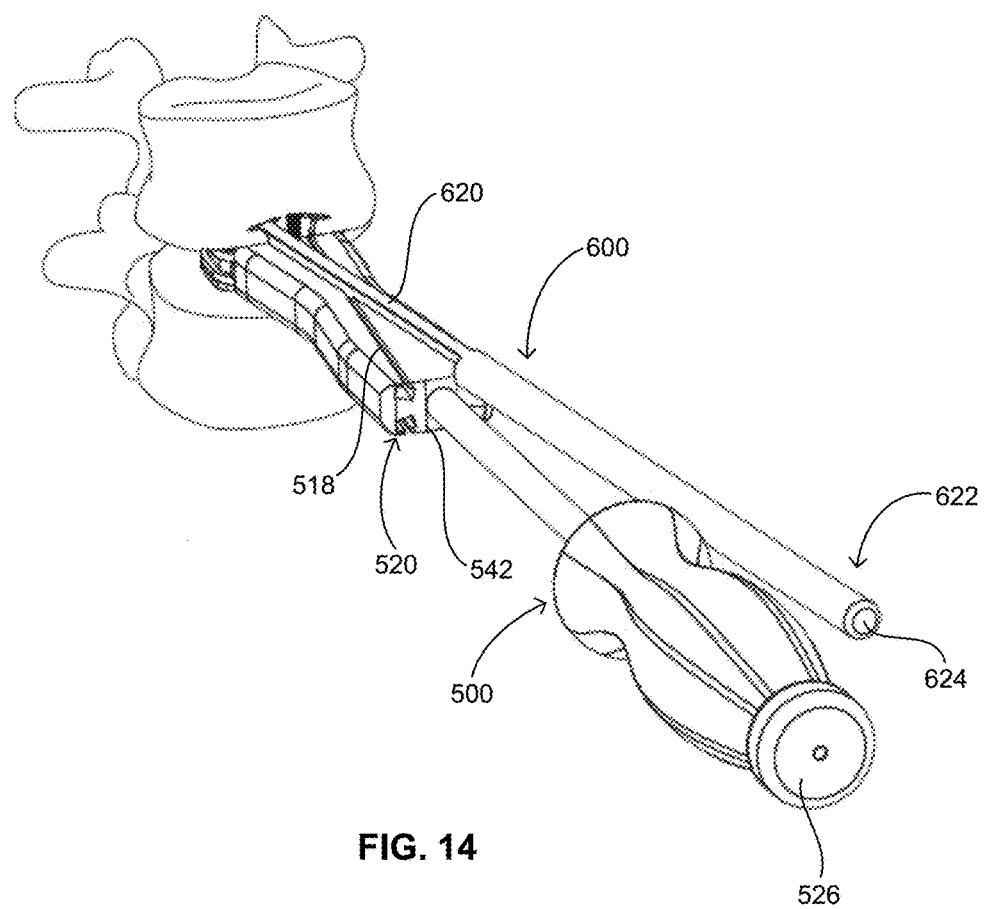
FIG. 14 is a perspective view of an anchor inserted in the intervertebral disc space by the inserter shown in FIG. 9 and the tamp shown in FIG. 12.
Figure 15:
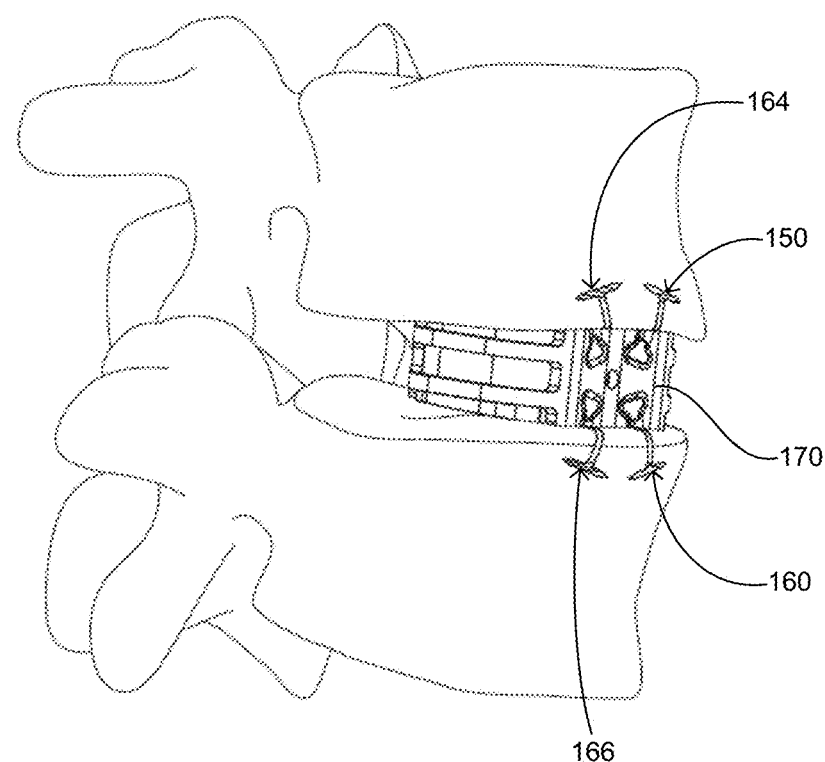
FIG. 15 is a perspective view of the implant shown in FIG. 13 and four anchors inserted into an intervertebral disc space between two adjacent vertebrae.
Figure 16:
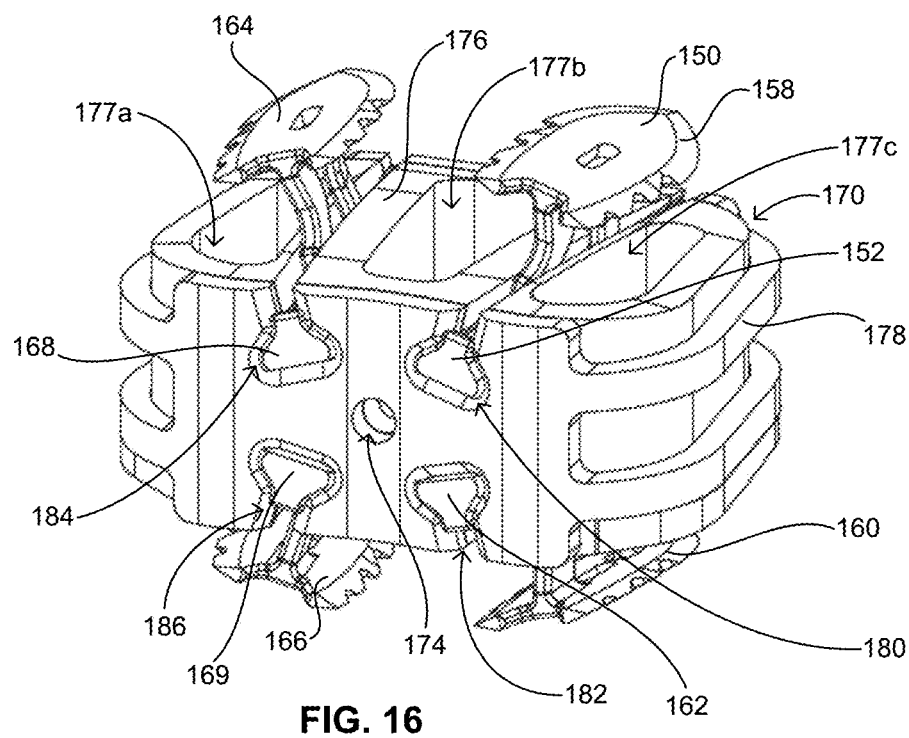
FIG. 16 is a perspective view of the implant and two anchors shown in FIG. 15.

In accordance with a second embodiment of the present invention, a set of instruments is shown in FIGS. 9-14 that are configured for installation of an implant 170 and anchors 150, 160, 164, 166 shown in FIGS. 15 and 16. The instruments include an inserter 500 and an anchor tamp 600.

With reference to certain aspects of the below-described instruments, FIGS. 15 and 16 show implant 170 and anchors 150, 160, 164, 166, which are similar in nearly all respects to the above-described implant 100 and anchors 130, 140, and which are also described more thoroughly in U.S. Non-Provisional patent application Ser. Nos. 12/640,816, 12/640,860, and 12/640,892. Implant 170 includes, for example, a spacer 176 and a jacket 178 disposed thereabout. Spacer 176 includes chambers 177a, 177b, 177c that can be packed with graft material. Anchor 150 is essentially identical to anchors 160, 164, 166 and is configured to engage the vertebral body and implant 170. In the implanted position, anchors 150, 164 are disposed on opposite sides of implant 170 from anchors 160, 166. Implant 170 includes interconnection features 180, 182, 184, 186 that extend across spacer 176 and jacket 178 to mate with interconnection portions 152, 162, 168, 169, of anchors 150, 160, 164, 166, respectively. Anchor 150 is generally elongate with a leading end and a trailing end opposite therefrom, with interconnection portion 152 extending therebetween. Interconnection portion 152 is shaped and sized to mate with interconnection feature 180 of implant 170. Anchor 150 further includes a fixation portion 158 configured as a plate extending between leading and trailing ends 154, 156. Anchor 150 also includes legs extending generally perpendicularly between interconnection portion 152 and fixation portion 158. The leading leg includes a cutting edge and a piercing tip capable of cutting through bone.

Figure 9:
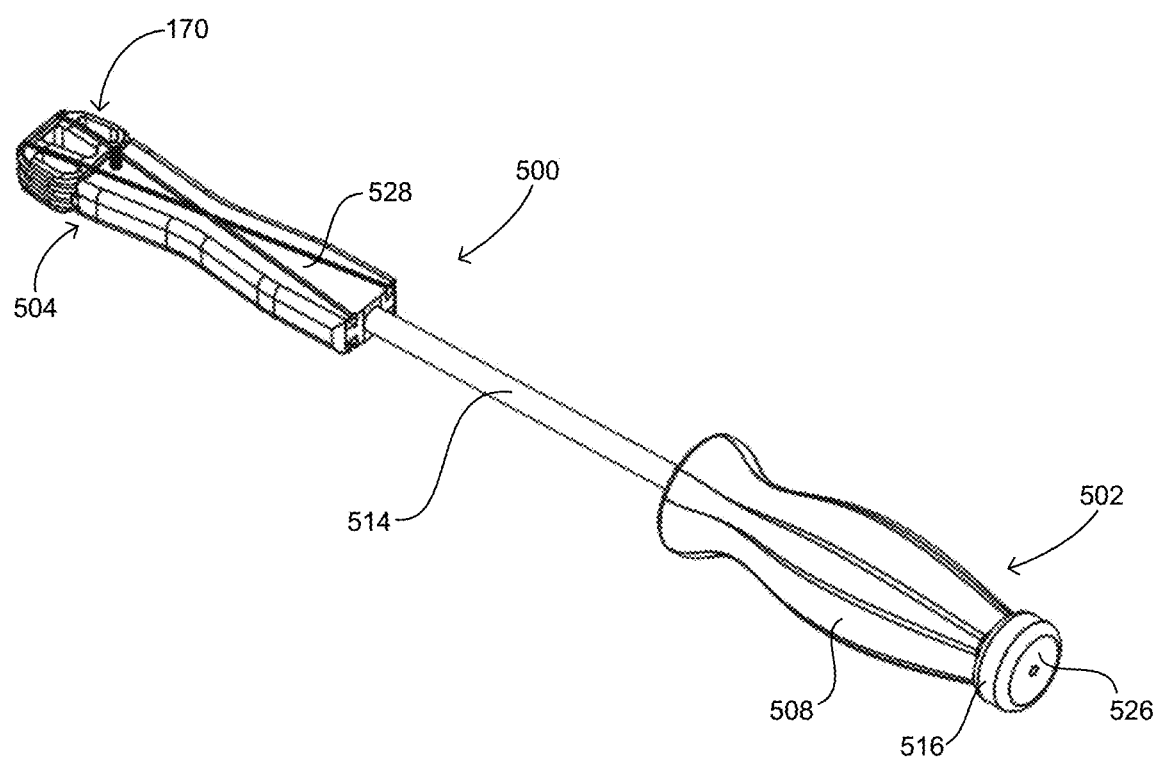
FIG. 9 is a perspective view of an implant connected to an inserter in accordance with a second embodiment of the present invention.
Figure 10:
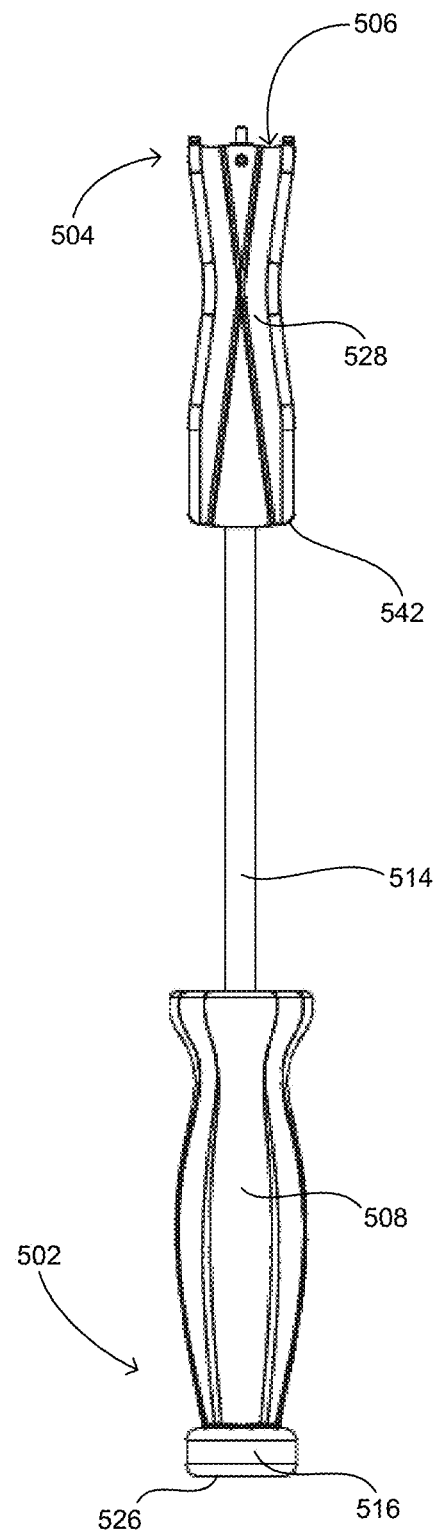
FIG. 10 is a top plan view of the inserter shown in FIG. 9.
Figure 11:
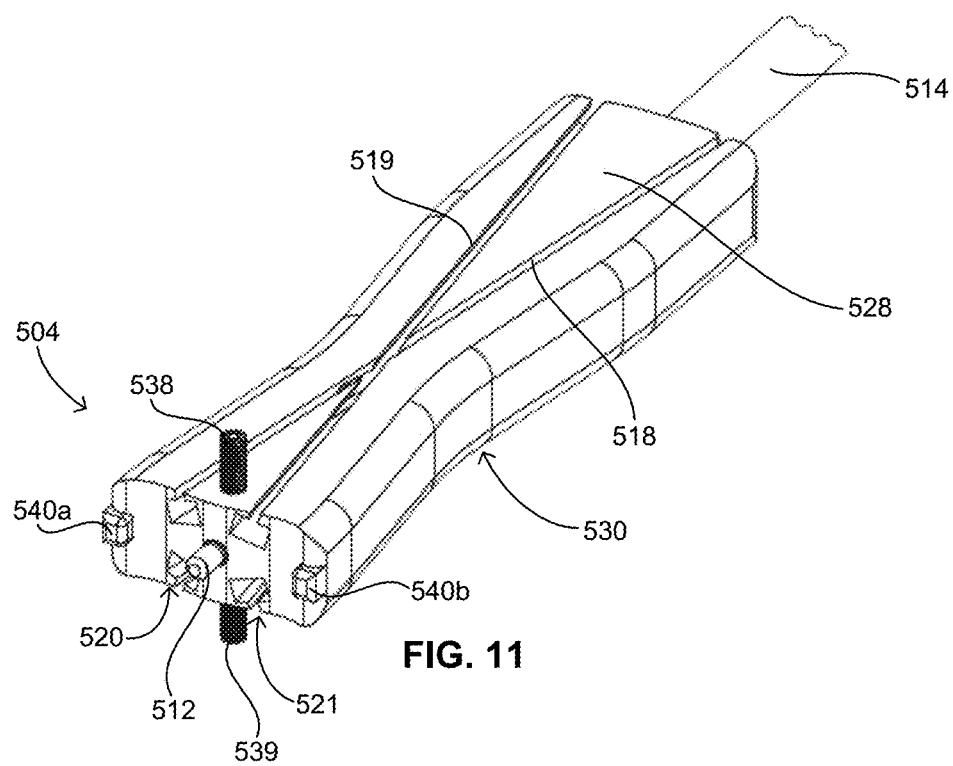
FIG. 11 is a perspective view of the distal end of the inserter shown in FIG. 9.

Shown in FIGS. 9-11, inserter 500 is capable of attaching securely to implant 170 and placing it into the intervertebral disc space, delivering the anchors 150, 160, 164, 166, and guiding anchor tamp 600. Inserter 500 is an elongate instrument that includes a body 514 having a proximal end 502 and a distal end 504. At distal end 504, inserter 500 includes a concavely-curved surface 506 that is preferably shaped to match the curvature of implant 170. Surface 506 can be planar or otherwise shaped to more accurately match the contours of the implant with which it is utilized. A threaded rod 512 runs through body 514 and is disposed between proximal end 502 and distal end 504 of inserter 500. Rod 512 extends distally of surface 506, is engageable with a threaded aperture 174 of implant 170, and is controlled by a rotatable knob 516 located at proximal end 502 of inserter 500 that allows the user to tighten implant 170 to surface 506 of inserter 500, thus securing implant 170 rigidly in all six degrees of freedom with respect to inserter 500. Tabs 540a, 540b also protrude from surface 506 and engage with corresponding portions of implant 170.

Proximal end 502 of inserter 500 includes a handle 508 and a large face 526 capable of withstanding blows from a mallet to facilitate insertion of implant 170 when impaction is required. A surgeon may grasp and control the instrument at handle 508 without his/her hand or fingers coming into contact with soft tissues of the cervical spine during use of inserter 500.

Inserter 500 has superior longitudinal channels 518, 519 and inferior longitudinal channels 520, 521 located on superior surface 528 and inferior surface 530, respectively, of inserter 500 and being capable of containing, aligning, and slidably delivering anchors 150, 160, 164, 166 to engage with implant 170 and the adjacent vertebral bodies once implant 170 is inserted into the disc space. The pairs of channels 518, 519, 520, 521 cross on their respective surfaces according to the orientation of the anchors 150, 160, 164, 166 with respect to implant 170. Of course, channels 518, 519, 520, 521 may be oriented with respect to their respective surface 528, 530 at any angle with surface 506, and may be crossed, angled, or parallel. Channels 518, 519, 520, 521 may also be angled with respect to their respective surface 528, 530 such that their depth extends along a direction that is perpendicular or angled or canted with their respective surface 528, 530. As shown in FIG. 11, channels 518, 519, 520, 521 are each angled with their respective surface 528, 530. The angles of channels 518, 519, 520, 521 correspond with the orientation of the interconnection features of the implant, and determine the final positioning of the anchors. Channels 518, 519, 520, 521 are also used to guide tamp 600 when tapping the respective anchor into implant 170 and the adjacent vertebra. Tamp 600 accesses channels 518, 519, 520, 521 at a proximal face 542 of distal end 504, shown more clearly in FIG. 14.

Also at its distal end 504, inserter 500 includes a post 538 on superior surface 528 and a similar post 539 on inferior surface 530. Posts 538, 539 are configured to engage with the adjacent vertebral bodies to provide a stop for preventing over-insertion of inserter 500. Each post 538, 539 is disposed on the respective superior and inferior surfaces 528, 530 so as not to cover or otherwise obstruct channels 518, 519, 520, 521.

Inserter 500 is preferably at least somewhat symmetrical about a horizontal plane parallel to and extending between superior and inferior surfaces 528, 530 such that inserter 500 may be utilized in the orientation depicted or in an inverted orientation. As implant 170 possesses a similar symmetry, inserter 500 can beneficially be connected with implant 170 in either orientation. Inserter 500 is also preferably at least somewhat symmetrical about a vertical plane that bisects superior and inferior surfaces 528, 530.

Inserter 500 is preferably constructed of metal, and may include two or more metals. For example, body 514 may be constructed of stainless steel while handle 508 is constructed of titanium, which may be color anodized. Of course any other material suitable for use during surgery may be employed in the construction of inserter 500. Preferably, the materials utilized in the construction of inserter 500 are capable of being sterilized multiple times, so that the inserter may be utilized in multiple surgeries/procedures.

Figure 12:
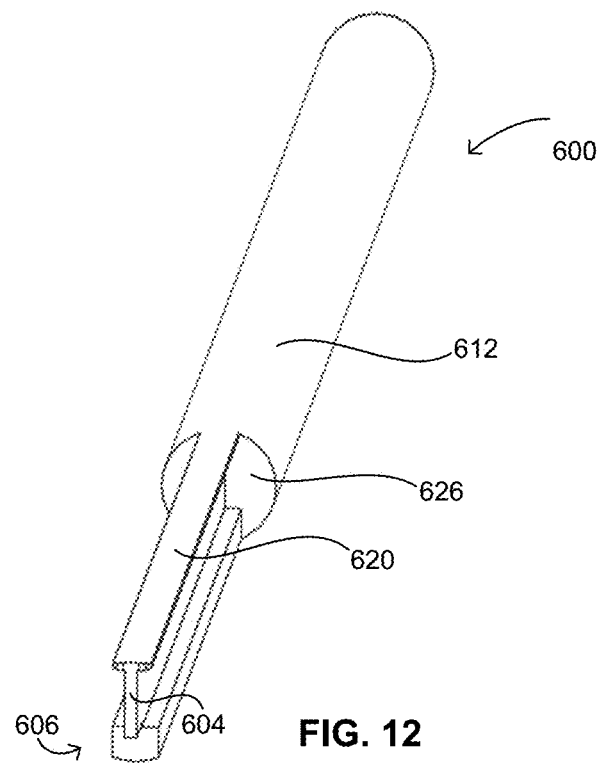
FIG. 12 is a perspective view of a distal end of a tamp in accordance with the second embodiment.

As shown in FIGS. 12 and 14, tamp 600 is a long instrument constructed preferably of stainless steel, and is used primarily for the insertion of anchors 150, 160, 164, 166 into the vertebral bodies. Tamp 600 includes a proximal end 622 and a distal end 606 with a lead edge 604 that may or may not match the conforming geometry on the proximal end of anchor 150. When assembled to the inserter 500, tamp 600 engages the proximal end of anchor 150 to controllably push anchor 150 into the vertebral body. The mating surfaces between tamp 600 and anchor 150 can be of any configuration as long as tamp 600 may push anchor 150 distally when force is exerted at proximal end 622.

Tamp 600 has a profile that allows it to fit within channels 519, 520, 521, 522. Thus, sliding engagement is permitted between tamp 600 and inserter 500 to control the path of tamp 600 during insertion. A stop face 626 is provided that separates a cutting portion 620 from a main body 612. Stop face 626 is configured to abut face 542 of inserter 500 during use of tamp 600 to prevent overinsertion of anchors 150, 160, 164, 166 into the vertebral bodies. Once mated with inserter 500, tamp 600 may be impacted similarly to the above described first embodiment on an impaction surface 624 at proximal end 622, as shown in FIG. 14. Impaction of surface 624 aids in forcing distal end 606 of tamp 600, and accordingly, anchors 150, 160, 164, 166 into the bone.

Figure 12A:
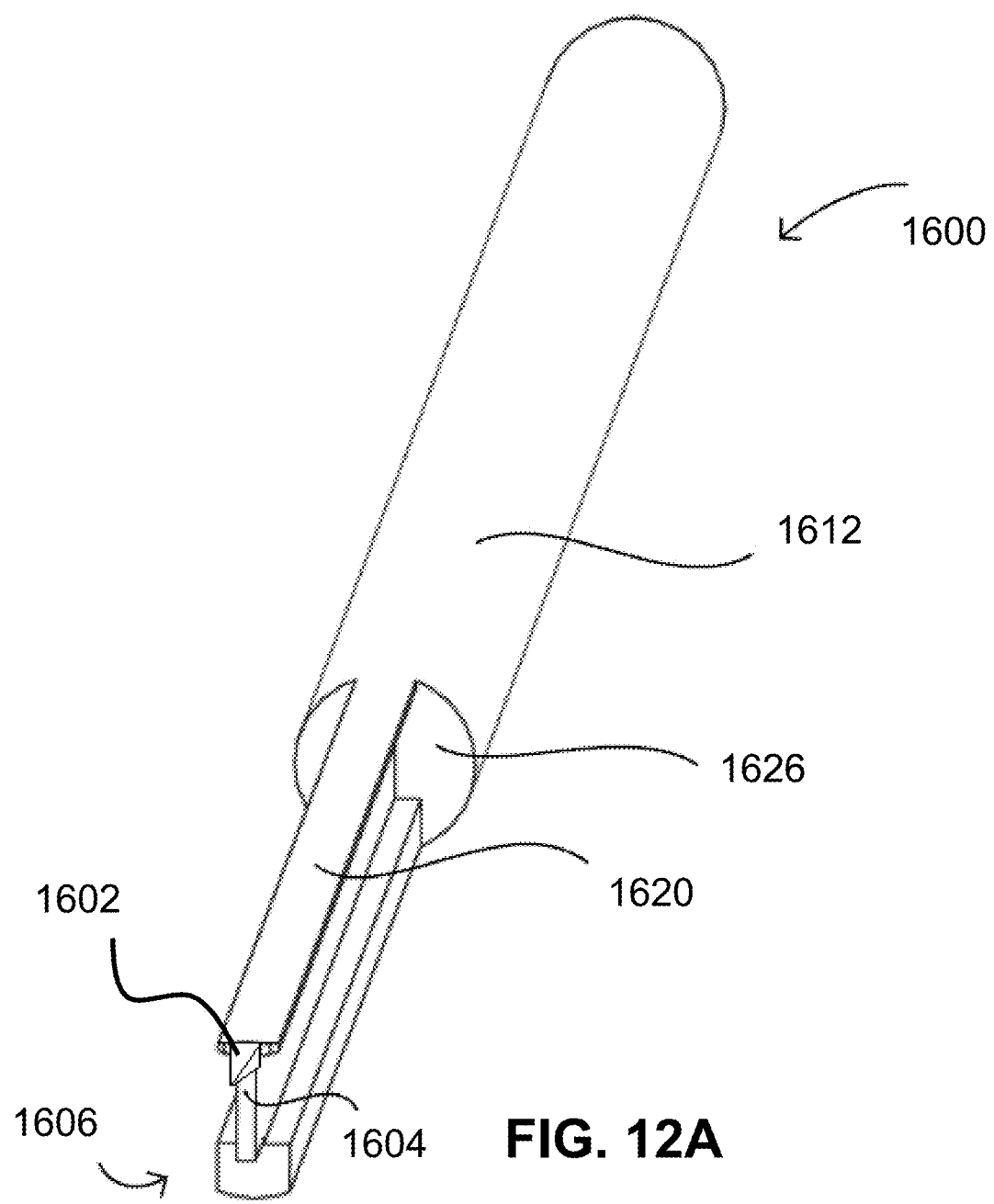
FIG. 12A is a perspective view of a distal end of a cutter in accordance with the second embodiment.
Figure 13:
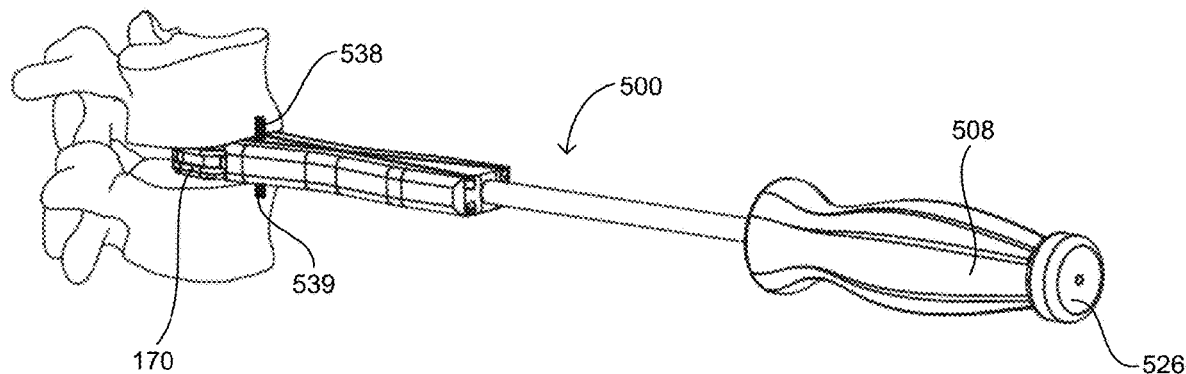
FIG. 13 is a perspective view of the implant attached to the inserter shown in FIG. 9 inserted into an intervertebral disc space between two adjacent vertebrae.

A cutter 1600 is depicted in FIG. 12A, and has a similar construction to tamp 600 with cutting edges and a needle tip 1602. Cutter 1600 includes a distal end 1606 with a lead edge 1604 that may or may not match the conforming geometry on the proximal end of anchor 150. A stop face 1626 is provided that separates a cutting portion 1620 from a main body 1612. Alternatively, tamp 600 may be provided with appropriate cutting edges to operate as both a cutter and a tamp. Of course, in such a case, the tamp would first be utilized to cut the bone and thereafter utilized to insert the anchors in place.

A method of inserting implant 170 is similar in nature to the method described with respect to the first embodiment. The method may begin with a surgeon being provided with a kit of differently sized and shaped implants and anchors and the surgeon selecting a particular implant and corresponding anchors according to the anatomy of the patient upon which the surgical procedure is to be performed. Selected implant 170 is then attached to distal end 504 of inserter 500. Preferably, threaded rod 512 is inserted into threaded aperture 174 to secure implant 170 to inserter 500 in a particular orientation. Threaded rod 512 may be screwed into aperture 174 by the surgeon actuating knob 516. Implant 170 and inserter 500 are now secured to one another such that manipulation of inserter 500 can ensure proper positioning of implant within the disc space.

The intervertebral disc space is prepared by removing at least a portion of the intervertebral disc material. This can be done at this stage of the procedure or prior to the surgeon's selection or attachment of implant 170. With the appropriate portion of the disc space cleared, the surgeon aligns and inserts implant 170 into the disc space by manipulating inserter 500, preferably at handle 508 to allow for the area adjacent the disc space to remain free and clear so that the procedure can be appropriately observed. If necessary, face 526 at proximal end 502 of inserter 500 may be impacted by a surgical mallet or other device to allow for proper insertion and position of implant 170 between the adjacent, often collapsed, vertebrae. Posts 538, 539 may contact the adjacent vertebral bodies to prevent overinsertion of implant 170. To further aid in fusing implant 170 to the adjacent vertebrae, one or more of chambers 177a, 177b, 177c may be packed with bone graft material prior to insertion of implant 170 within the disc space.

At this point, cutter 1600 or, if tamp is provided with the appropriate blades, tamp 600 may be used to cut entryways into the adjacent vertebrae (if so designed). This step is not necessary, as anchors 150, 160, 164, 166 are configured to pierce the uncut bone.

Anchor 164 is then loaded into longitudinal channel 519, which can also be described as a track on superior surface 528. The method of inserting an anchor according to the present invention is herein described with respect to anchor 164, although more than one anchor may be inserted simultaneously. Interconnection element 152 is disposed within channel 519, and tamp 600 is slidably attached to inserter 500 proximal of anchor 164 within channel 519 as well, with least lead edge 604 in contact with the trailing end of anchor 164. As tamp 600 is advanced toward the vertebra, it forces anchor 164 along with it and eventually into contact with the bone. Tamp 600 is further advanced to fully insert anchor 164 into the vertebra such that the interconnection element of anchor 164 locks into place within interconnection feature 184 of implant 170. Stop face 626 may abut surface 542 of inserter 500 during advancement to ensure that anchor 164 is not over-inserted. Anchor 164 is eventually seated such that migration and backout are prevented between anchor 164 with respect to both implant 170 and the adjacent vertebra. Thus, axial and torsional movement between implant 170 and the adjacent vertebra are prevented.

Anchors 150, 160, 166 may be inserted in the same manner as described above, although with respect to different channels of inserter 500. Tamp 600 may be used first on a one anchor and subsequently on the others, or two or more tamps 600 may be utilized together. It is noted that tamp 600 is generally restrained in 5 degrees of freedom with respect to inserter 500 during insertion.

After tamp 600 is disengaged from inserter 500, threaded rod 512 is unthreaded from implant 170 using knob 516. Inserter 500 is then removed from the surgical site, leaving implant 170 and anchors 150, 160, 164, 166 in position as shown in FIG. 15. When implant 170 and anchors 150, 160, 164, 166 are implanted from an anterior approach, as shown in FIG. 15, the leading portion of jacket 178 is positioned in the posterior portion of the intervertebral disc space and the trailing portion of jacket 178 is positioned in the anterior portion of the intervertebral disc space. In this arrangement, prosthesis implant 170 and anchors 150, 160, 164, 166 may replicate the strength and stiffness of the natural anterior and posterior longitudinal ligaments to provide superior fixation of adjacent vertebral bodies.

The instruments according to the present invention are preferably constructed of metal, although other types of materials may be used that give the proper strength to the instruments. Such materials could be hard polymeric materials or other plastics. Of course any other material suitable for use during surgery may be employed in the construction of any of the instruments. Preferably, the materials utilized are capable of being sterilized multiple times, so that the instruments may be utilized in multiple surgeries/procedures.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention enjoys wide industrial applicability including, but not limited to, systems and methods including surgical instruments for implantation of intervertebral implants.

The invention claimed is:

1. A method of inserting an implant in the intervertebral disc space between two adjacent vertebrae and an anchor engageable with the implant and an adjacent vertebra, the method comprising the steps of:
　attaching a distal end of an inserter to the implant;
　inserting the implant into the disc space by manipulating the inserter; and
　cutting an entryway into the adjacent vertebra for the anchor, including sliding a cutter along the inserter and piercing the adjacent vertebra; and
　inserting the anchor along a track exposed at a surface of the inserter and into engagement with the implant and the adjacent vertebra, such that while the anchor is disposed within the track, the anchor extends above the surface as it translates along the inserter.

2. The method of claim 1, further comprising a step of sliding a tamp along the inserter in contact with the anchor to force the anchor into engagement with the implant and the adjacent vertebra.

3. The method of claim 2, wherein the step of sliding the tamp includes impacting a proximal end of the tamp.

4. The method of claim 1, further comprising a step of impacting a proximal end of the instrument that is in contact with the anchor.

5. The method of claim 1, further comprising a step of applying an impaction force to the anchor.

6. The method of claim 1, wherein the step of attaching includes securing the implant to the distal end of the inserter by inserting a rod of the inserter into an aperture of the implant.

7. The method of claim 6, wherein the step of inserting the rod includes screwing a threaded portion of the rod into a threaded portion of the aperture.

8. The method of claim 1, wherein the step of inserting the implant includes impacting a proximal end of the inserter.

9. The method of claim 1, wherein the step of inserting the anchor includes locking the anchor to the implant to prevent migration and backout of the anchor with respect to the implant.

10. The method of claim 1, wherein the step of inserting the anchor includes locking the anchor to the adjacent vertebra to prevent migration and backout of the anchor with respect to the adjacent vertebra.

11. The method of claim 1, wherein the anchor prevents axial movement along an axis of the spine between the implant and the adjacent vertebra.

12. The method of claim 1, wherein the anchor prevents torsional movement between the implant and the adjacent vertebra.

13. The method of claim 1, further comprising a step of inserting a second anchor into engagement with the implant and the opposing adjacent vertebra.

14. The method of claim 13, further comprising a step of cutting an entryway into the opposing adjacent vertebra for the second anchor.

15. The method of claim 14, further comprising a step of inserting third and fourth anchors into engagement with the implant and adjacent vertebrae such that two anchors are engaged at a superior surface of the implant and two anchors are engaged at an inferior surface of the implant.

16. The method of claim 1, further comprising steps of:
　providing a kit of differently sized and shaped implants and anchors; and
　selecting an implant and an anchor according to the anatomy of the patient.

* * * * *